United States Patent [19]

Berg et al.

[11] Patent Number: 5,492,004

[45] Date of Patent: Feb. 20, 1996

[54] MEASUREMENT OF HYDROGEN LEAKAGE THROUGH STATOR WINDINGS INTO GENERATOR COOLANT WATER AND OXYGENATION OF THE COOLANT WATER

[75] Inventors: Hans E. Berg, Ann Arbor, Mich.; Lawrence E. Jordan, Amsterdam, N.Y.

[73] Assignee: General Electric Co., Schenectady, N.Y.

[21] Appl. No.: 329,737

[22] Filed: Oct. 26, 1994

[51] Int. Cl.$^6$ ............................. G01M 3/30; H02K 9/24; G01N 31/08

[52] U.S. Cl. ........................................ 73/40.70; 73/40.5 R

[58] Field of Search ............................... 73/40.5 R, 40.70

[56] References Cited

U.S. PATENT DOCUMENTS

| | | | |
|---|---|---|---|
| 3,248,297 | 4/1966 | Moore et al. | 73/40.7 |
| 3,894,138 | 7/1975 | Klaar | 310/53 |
| 4,216,821 | 8/1980 | Robin | 165/11 R |
| 4,226,113 | 10/1980 | Pelletier et al. | 73/40.7 |
| 4,319,479 | 3/1982 | Iwamura et al. | 73/19 |
| 4,321,110 | 3/1982 | Nickel et al. | 376/250 |
| 4,440,017 | 4/1984 | Barton et al. | 73/40.5 R |
| 4,898,021 | 2/1990 | Weaver et al. | 73/40.7 |

*Primary Examiner*—Hezron E. Williams
*Assistant Examiner*—J. David Wiggins
*Attorney, Agent, or Firm*—Nixon & Vanderhye

[57] ABSTRACT

Hydrogen leakage from a generator core through stator windings into the generator coolant water is measured by flowing air into the coolant water exiting the stator windings and measuring the hydrogen content of the gas vented from a coolant water reservoir. The flow of air into the coolant water also oxygenates the coolant water to prevent undesirable formation of less stable cuprous oxide layers and enhance the formation of a protective cupric oxide film on the inside surfaces of the copper stator windings. In another form, trace gas is introduced into one of the generator core environment and the coolant water and a detector measures the magnitude of the trace gas leaked between the generator core environment and the coolant water as an indication of the magnitude of hydrogen leakage escaping from the generator core into the stator water coolant system.

9 Claims, 2 Drawing Sheets

1

MEASUREMENT OF HYDROGEN LEAKAGE THROUGH STATOR WINDINGS INTO GENERATOR COOLANT WATER AND OXYGENATION OF THE COOLANT WATER

TECHNICAL FIELD

The present invention relates to methods of measuring hydrogen leakage through the stator windings of a generator into the generator coolant water and oxygenating the coolant water. Particularly, the present invention relates to methods of determining hydrogen leakage from a generator core environment into the coolant water flowing through the stator windings of the generator, as an indication of potential electrical insulator damage, while simultaneously oxygenating the coolant water.

BACKGROUND

The stator bar windings of generators of a certain size are typically water-cooled. That is, water flows from an inlet coolant water header into flow passages within the hollow copper strand stator bars and then flows outwardly of the generator into an outlet coolant header for flow into a reservoir. The coolant water is supplied the windings via a closed loop system including a heat exchanger and a deionizer. Leaks in the stator windings of water-cooled generators, for example, at the brazed joints of the windings, can eventually cause insulation damage that can affect the reliability and longevity of the unit. Early detection of such water leakage enables strategic testing and repair to be scheduled during minor outages, avoiding costly surprise replacements and extended outages. If early insulation damage is not discovered, the problem can quickly compound itself, as stator components are subject to thermal shock, cycling, corrosion and mechanical vibrations. This harsh environment causes and exacerbates leaks at a variety of locations, though most commonly at series loops and other brazed connections.

It will be appreciated that in water-cooled generators, a cooling core hydrogen environment is normally maintained at a higher pressure than the coolant water flowing through the stator windings. This pressure difference, combined with stator component permeability, particularly at the brazed joints, causes a slight, barely detectable, flow of hydrogen into the coolant water under normal operating conditions even in a leak-free generator. However, when leaks actually develop, the quantity of hydrogen flowing into the coolant water increases dramatically. By continuously or periodically monitoring the leakage flow of hydrogen into the coolant water, upward trending or step increases in the volume of hydrogen leakage can be used as a reliable indicator of water leaks and the potential for electrical insulation damage.

An additional concern involves the oxygenation level of the coolant water. With proper aeration, a tenacious and protective cupric oxide film advantageously forms on the inside surfaces of the copper windings. However, when the coolant water oxygen level drops, a less stable cuprous oxide layer is formed along these surfaces. This layer tends to break away from the winding surface, sloughing off base copper and introducing particles into the system. Oxygenation of the coolant water for generators is currently provided by air exchange through a vent line from the coolant water storage tank or reservoir to the atmosphere. Unfortunately, air in this line is relatively stagnant and the typical long length of the line, upwards of hundreds of feet in some installations, makes oxygen exchange difficult. Furthermore, significant hydrogen leaks may cause a constant outward flow of gas through this line, thus totally isolating the water from fresh air.

Present on-line testing techniques typically involve a technician climbing to the location where the water storage tank vent exits the building housing the generator. A polyethylene bag is secured over the vent and flow rate is determined by timing the period required to fill the bag. A hand-held flammable gas sensor is then placed in the bag to determine hydrogen content. Such test results are marginal and limited to the time of collection. Their value is thus questionable.

DISCLOSURE OF THE INVENTION

According to the present invention, there is provided a stator leak monitoring system which gives an on-line indication of a generator stator bar insulation condition, i.e., a winding leak, by measuring the volume of hydrogen escaping from the generator core into the stator bar water cooling system. The system also simultaneously oxygenates the coolant water by flowing air into the coolant water. More particularly, the stator leak monitoring system hereof measures the volume of hydrogen that leaks from the generator core into the stator coolant water and uses this data as an indication of potential stator bar insulation damage. To accomplish the foregoing, an opening to the atmosphere is provided in the closed coolant water system adjacent the top of the generator where the coolant water exits the stator windings. At this location, coolant water flowing downwardly into the water reservoir creates a low-pressure area that induces an inward flow of air, i.e., air is aspirated into the coolant water. The exit flow through the vent for the reservoir is unidirectional but is not stable enough to be measured. Therefore, in accordance with the present invention, air flow into the system is measured and the percentage of $H_2$ in the gas exiting through the vent is determined whereby the total volume of $H_2$ leaking out the vent can be ascertained. Thus, the volume of hydrogen leaking or escaping from the generator core can be determined as follows:

$$H_{2\,(VOL)} = \frac{\% H_2}{1 - \% H_2} \text{ (Inflow) } (k) \text{ where}$$

% $H_2$ is the fraction of $H_2$ measured in the gas exiting the reservoir vent to atmosphere; Inflow is the rate of fresh air flowing into the system; and k is a conversion factor. Secondly, the inflow of air provides fresh air to mix with the coolant water as the water returns to the reservoir. This ensures that the coolant water has sufficient oxygen levels to avoid undesirable oxide formation on the winding surfaces. By locating a hydrogen gas analyzer for sampling gas flowing through the reservoir vent and locating a gas (air) flow meter at the inlet opening for the air into the system, the quantity of hydrogen in the vented gas stream can be measured as a percentage of total flow. Thus, the escaping hydrogen volume may be determined and the data interpreted as an indication of cooling system leaks. While this system may not differentiate between the existence of one or more small leaks or a major leak, the main advantage is that the data may be recorded while the generator is on-line and operating. This enables planning for additional tests and ultimately a reduction in outage time. Additionally, an oxygen analyzer may also be incorporated in the system in the coolant water reservoir in order to ensure sufficient oxygen levels are maintained. Thus, it will be appreciated that the outputs from the flow meter and gas analyzers may be continuously or periodically displayed, providing an indication of hydrogen leakage and hence any potential insulation damage, as well as oxygen levels. The system may also include an alarm that will be activated in the event of a rapid increase in escaping hydrogen, thus signalling large leaks.

While the foregoing aspect of the present invention provides an indication of potential insulation damage as a result of coolant lo leakage, very small hydrogen leaks alone may be difficult to detect because gas escaping through a small leak will be masked by a baseline amount that leaks even in a sound generator. That is, due to the high permeability of the materials and a pressure drop across the generator core environment and the stator coolant water, gas leaks on is a very small order, e.g., 1–2 cubic feet per day, occur even in a leak-free generator. To counter this potential inability to detect very small leaks, the present invention in another aspect provides for the addition of a trace gas of a certain critical molecular size into either the generator core or the coolant water. A detector of the trace gas is located in the other region and hence when the trace gas is detected, it can be determined if the low hydrogen readings are due exclusively to permeation or if a finite size leakage hole exists. Preferably, the trace gas is injected into the generator core environment and will follow the same leakage path into the coolant water as does the hydrogen. While the trace gas can be introduced continuously during generator operation, substantial quantities of make-up trace gas would be required due to leaks from other generator components such as the oil seals. Accordingly, the trace gas test is preferably non-continuous or periodic in order to conserve trace gas.

In a preferred embodiment according to the present invention, there is provided a method of measuring hydrogen leakage from a generator core into generator coolant water flowing through the stator windings comprising the steps of providing a core hydrogen environment within the generator, flowing coolant water from a coolant water inlet through the generator stator windings to a coolant water reservoir, flowing air into the coolant water exiting the stator windings, measuring the air flowing into the coolant water, venting gas from the coolant water reservoir and measuring the hydrogen content of the gas vented from the reservoir whereby the magnitude of hydrogen leakage from the generator core environment through the stator windings into the generator coolant water can be determined.

In a further preferred embodiment according to the present invention, there is provided a method of enhancing the oxygen content of coolant water flowing through stator windings of a generator comprising the steps of flowing coolant water from a coolant water inlet through the generator stator windings to a coolant water reservoir, flowing air into the coolant water exiting the stator windings to enhance the formation of a protective oxide film on the surfaces of the stator windings and recirculating the water from the reservoir through the stator windings.

In a still further preferred embodiment according to the present invention, there is provided a method of detecting hydrogen leaks from a generator core into generator coolant water flowing through the stator windings comprising the step of introducing a trace gas into one of the generator core or the coolant water and detecting the presence of the trace gas from another of the generator core or the coolant water to thereby indicate the magnitude of leakage between the generator core and the coolant water.

Accordingly, it is a primary object of the present invention to provide, in a generator, a hydrogen leak detection system for measuring the magnitude of hydrogen leakage from the generator core into the stator coolant water to provide an indication of the potential stator windings insulation damage and also to oxygenate the coolant water.

BEST MODE FOR CARRYING OUT THE INVENTION

Figure 1:
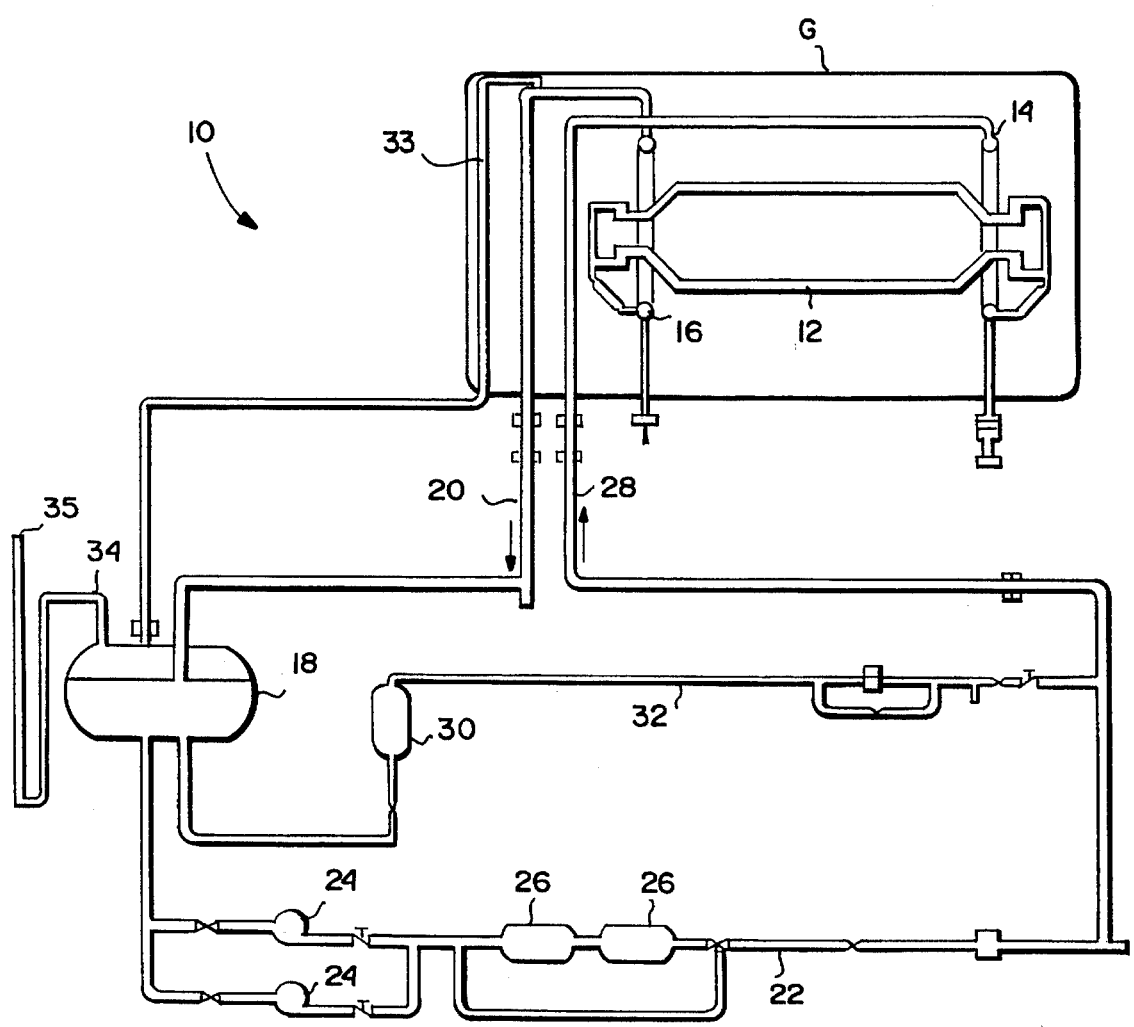
FIG. 1 is a schematic representation of a known water cooling system for a generator.

Referring now to the drawings, particularly to FIG. 1, there is illustrated a water cooling circuit, generally designated 10, for a generator G. As well known, generator G includes a plurality of hollow stator bar windings through which water is circulated for cooling purposes. The cooling circuit through the stator bar windings is schematically illustrated at 12 and includes a water coolant inlet header 14 and a water coolant outlet header 16. The water coolant exiting the outlet header 16 is connected to a reservoir 18 by a water coolant return line 20. A water coolant supply line 22 supplies coolant water via pumps 24 and heat exchangers 26 to a water coolant inlet line 28 directly connected to the inlet header 14. A portion of the coolant water from the reservoir 18 flows through a deionizer 30 in a bypass line 32 which joins the water coolant supply line 22 downstream of heat exchangers 26. As a consequence of this arrangement, water coolant flows through the stator bar windings in a closed circuit.

Typically, a vent line 33 is disposed at the top of the generator tapped into the water coolant return line 20, the opposite end being connected to the reservoir 18. Vent line 33 is used to break any vacuum in line 20. Additionally, a vent line 34 is connected between the reservoir 18 and a suitable vent opening 35 at the site of the generator for venting the gases above the coolant in the reservoir 18. The vent opening 35 is often spaced a substantial distance, on the order of hundreds of feet, from reservoir 18. While some oxygenation of the water as a result of air inlet through the vent 35 and vent line 34 into the reservoir does occur, the distance between the reservoir and the vent renders any substantial oxygenation of the coolant water at very modest levels. Moreover, if there is a net hydrogen leakage into the water coolant system, the venting of gases from the reservoir would afford substantially a one-way flow from the reservoir to the vent without a reverse flow air for water coolant oxygenation purposes. Additionally, systems of this type typically do not have any mechanisms for indicating potential stator bar winding insulation damage within the generator.

Figure 2:
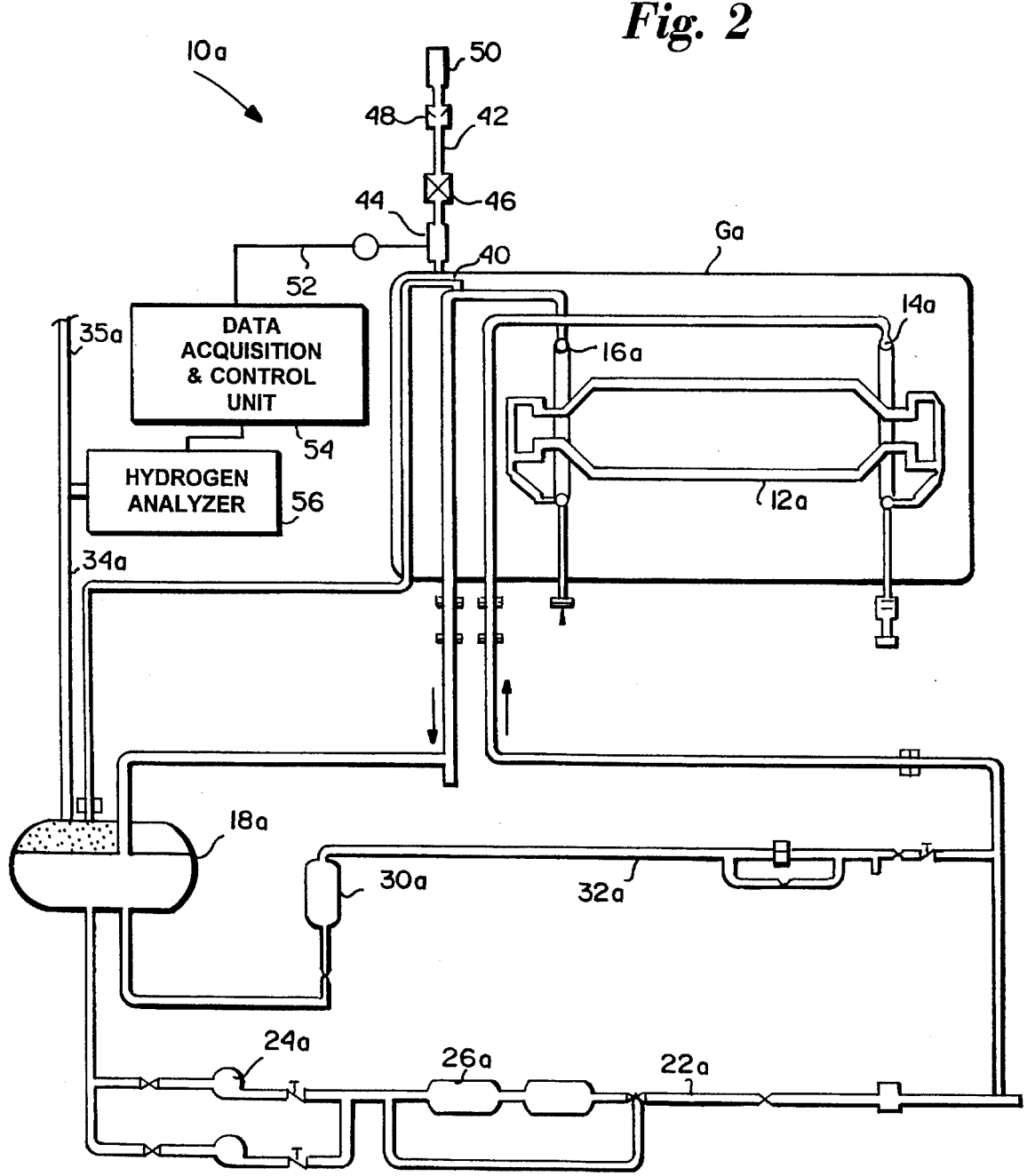
FIG. 2 is a schematic representation of a water cooling system for a generator employing the methods of the present invention.

Referring now to FIG. 2, wherein like parts are indicated by like reference numerals followed by the suffix "a," there is illustrated a closed-circuit water coolant system 10a for the generator Ga with the addition of a system for detecting hydrogen leakage from the stator bar winding core environment into the water coolant, e.g., hydrogen leakage through the brazed joints of the end loop connections of the windings. As indicated previously, detection of the magnitude of hydrogen leakage affords an indication of leakage of water from the stator bar windings and, hence, an indication of potential damage to the generator insulation. To accomplish this, the present invention provides an opening 40 to atmosphere at the water coolant exit or return line 20a from the outlet header. At the location of the opening 40, the coolant water flows downwardly to the reservoir 18a, creating a low-pressure area that induces an inward flow of air. That is, the flow of coolant water from the outlet header 16a to the reservoir 18a aspirates air through the opening 40 into the outlet flow line 20a. The opening may be provided in a line 42 having is a flow meter 44, a gate valve 46, a check valve 48 and a filter 50. The flow meter 44 measures the flow rate of air aspirated in the system and is coupled by an electrical output line 52 to a data acquisition and control unit 54. The opening 40 serves two purposes: (1) it increases the flow of gases from the reservoir through the vent line 34a such that the flow through the vent line will be unidirectional, enabling the percentage of $H_2$ and thus the escaping hydrogen volume to be determined; and (2) the inflow of fresh air mixes with the coolant water as the water returns to the storage tank, thereby oxygenating the coolant water and providing sufficient oxygen levels to provide undesirable oxide formation on the interior surfaces of the windings. Also as illustrated in FIG. 2, a hydrogen analyzer 56 continuously samples the gas in vent line 34a exiting the system through vent 35a. Analyzer 56 measures the percentage of hydrogen in the air flowing through vent line 34a.

In operation, the flow rate of air into the system through opening 40 is measured by the flow meter and the hydrogen analyzer measures the percentage of hydrogen in the air flowing through the vent line 34a. Knowing that the total flow through the vent line 34a is equal to the air flow plus the hydrogen flow and that the hydrogen flow is a percentage of the total flow, the data acquisition unit 54 can compute the volume of hydrogen escaping into the otherwise closed stator cooling system. That is, the data acquisition unit 54 receives signals from the flowmeter 44 and the hydrogen analyzer 56 corresponding to the range of flow and range of hydrogen concentration, respectively. Unit 56 then calculates the volume flow rate of hydrogen by solving the equations:

Total Flow Through Vent 35a ($Qt$)=Air Flow ($Qa$)+Hydrogen Flow ($Qh$)

and $Qh$=Hydrogen Concentration (% $H_2$)×$Qt$.

Qa and % $H_2$ are known measurements and the two equations can be solved for Qt and Qh. Thus, the escaping hydrogen volume is determined and the data is interpreted for possible cooling system leaks. It will be appreciated that the data interpretation will not be able to differentiate between a number of small leaks or a single large leak. However, the system affords the very distinct advantage of determining the magnitude of hydrogen leakage while the generator is operating and on-line. This is particularly advantageous in affording a running indication of potential insulation damage should the magnitude of the detected hydrogen trend upwardly.

In the foregoing described system for assessing potential insulation damage, it will be appreciated that there is a very small gas leakage, for example, on the order of 1–2 cubic feet per day, even in a leak-free generator. As a consequence, it is difficult to detect very small leaks using hydrogen alone because the gas escaping through a small leak will be masked by the baseline quantity that leaks, even in a sound generator. To accommodate this, a trace gas of a certain molecular size, e.g., a perfluorocarbon, hydrogen hexafluoride, may be introduced into either the generator core or the coolant water. A trace gas detector is then placed in the other of the generator core or the coolant water and thus the system will be able to determine if a finite size leakage path exists.

If the detector is in the generator core, gas will be sampled similarly as is the hydrogen detected in the previous embodiment. If the gas is injected into the generator core, then the detector will either be located in the water or in the space above the water in the reservoir 18a. If the trace gas detector is located above the reservoir, the same sampling flow as the hydrogen analyzer will be used. Preferably, the flow will pass through a condenser before the hydrogen analyzer and thus be free of any moisture. In any event, the trace gas detector will be capable of continuously sending a yes/no signal to the hydrogen leak detection system data acquisition unit. While it is preferable to inject the trace gas into the generator core where the trace gas will follow the hydrogen leakage path, this method of operation requires potentially sizable trace gas make-up due to leaks out of other generator components, such as the oil seals. Thus, while the trace gas test may be used on a continuous basis, it is preferable to use the trace gas test on a non-continuous or periodic basis to conserve trace gas supplies.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A method of measuring hydrogen leakage from a generator core into generator coolant water flowing through the generator stator windings comprising the steps of:

providing a core hydrogen gas environment within the generator;

flowing coolant water in a flowpath leading from a coolant water source inlet, then through the generator stator windings and a conduit to a coolant water reservoir;

flowing a measurable amount of air into said conduit and the coolant water after the coolant water exits the stator windings;

measuring the quantity of air flowing into said conduit and into the coolant water;

venting gas through a vent line from the contained vapor space over the coolant water within said coolant water reservoir; and measuring the hydrogen content of the gas vented from the reservoir;

whereby the magnitude of hydrogen leakage from the generator core environment through the stator windings into the generator coolant water can be determined by the presence of an abnormally higher concentration of hydrogen gas in the gas vented from the vapor space within said coolant water reservoir.

2. A method according to claim 1 wherein the step of flowing air into the coolant water includes inducing the flow of air through an opening into said conduit and the coolant water by creating a low-pressure area in the flowpath of the coolant water within said conduit leading to the coolant water reservoir, the opening into the conduit being exposed to atmosphere.

3. A method according to claim 1 wherein the step of measuring includes providing a hydrogen gas analyzer in said vent line for sampling the gas vented from the reservoir to determine the fraction of hydrogen therein.

4. A method according to claim 1 wherein the step of measuring is accomplished during operation of the generator.

5. A method according to claim 1 including increasing the oxygen content of the coolant water by flowing the air into the coolant water to inhibit the formation of undesirable oxides on internal surfaces of the stator windings.

6. A method according to claim 1 including introducing a trace gas into one of the generator core or the coolant water and detecting the presence of the trace gas in another of the generator core or the gases vented from the coolant water to indicate the magnitude of leakage between the generator core and the coolant water.

7. A method of enhancing the oxygen content of coolant water flowing through coolant stator windings of a generator comprising the steps of:

provide, flowing coolant water in a flowpath leading from a coolant water source inlet, then through the generator stator windings and a conduit to a coolant water reservoir;

flowing a measurable amount of air into said conduit and the coolant water after the coolant water exits the stator windings to enhance the formation of a protective oxide film on the surfaces of the stator windings; and recirculating the water from the reservoir through the coolant stator windings.

8. A method according to claim 7 including introducing a trace gas into one of the generator core or the coolant water and detecting the presence of the trace gas from another of the generator core or the coolant water to indicate the magnitude of leakage between the generator core and the coolant water.

9. A method of measuring hydrogen leakage from a generator core into generator coolant water flowing through the generator stator windings comprising the steps of:

providing a core hydrogen gas environment within the generator;

flowing coolant water in a flowpath leading from a coolant water source inlet, then through the generator stator windings and a conduit to a coolant water reservoir;

flowing a measurable amount of air into the coolant water;

measuring the quantity of air flowing into the coolant water;

venting gas through a vent line from the contained vapor space over the coolant water within said coolant water reservoir; and measuring the hydrogen content of the gas vented from the reservoir;

whereby the magnitude of hydrogen leakage from the generator core environment through the stator windings into the generator coolant water can be determined by the presence of an abnormally higher concentration of hydrogen gas in the gas vented from the vapor space within said coolant water reservoir.

* * * * *